(12) United States Patent
Gerard et al.

(10) Patent No.: US 9,301,733 B2
(45) Date of Patent: Apr. 5, 2016

(54) SYSTEMS AND METHODS FOR ULTRASOUND IMAGE RENDERING

(71) Applicant: General Electric Company, Schenectady, NY (US)

(72) Inventors: Olivier Gerard, Horten (NO); Stein Inge Rabben, Oslo (NO); Erik Normann Steen, Moss (NO)

(73) Assignee: General Electric Company, Schenectady, NY (US)

( * ) Notice: Subject to any disclaimer, the term of this patent is extended or adjusted under 35 U.S.C. 154(b) by 434 days.

(21) Appl. No.: 13/732,052

(22) Filed: Dec. 31, 2012

(65) Prior Publication Data

US 2014/0187948 A1 Jul. 3, 2014

(51) Int. Cl.
*A61B 8/08* (2006.01)
*A61B 8/00* (2006.01)

(52) U.S. Cl.
CPC .............. *A61B 8/5207* (2013.01); *A61B 8/0841* (2013.01); *A61B 8/465* (2013.01); *A61B 8/466* (2013.01); *A61B 8/467* (2013.01); *A61B 8/469* (2013.01); *A61B 8/483* (2013.01); *A61B 8/4405* (2013.01); *A61B 8/4427* (2013.01)

(58) Field of Classification Search
CPC .... G06T 7/0012; G06T 7/2207; A61B 5/055; A61B 5/506; A61B 5/726
See application file for complete search history.

(56) References Cited

U.S. PATENT DOCUMENTS

| | | | |
|---|---|---|---|
| 2004/0081340 A1 | 4/2004 | Hashimoto | |
| 2005/0049494 A1 | 3/2005 | Gritzky et al. | |
| 2007/0276225 A1* | 11/2007 | Kaufman et al. | 600/416 |
| 2008/0004521 A1* | 1/2008 | Hundley et al. | 600/414 |
| 2009/0306504 A1 | 12/2009 | Arai et al. | |
| 2010/0130860 A1 | 5/2010 | Yamagata | |
| 2011/0172531 A1 | 7/2011 | Kanayama et al. | |

FOREIGN PATENT DOCUMENTS

| | | |
|---|---|---|
| CN | 1493258 A | 5/2004 |
| CN | 1589747 A | 3/2005 |
| CN | 101351156 A | 1/2009 |
| CN | 102119865 A | 7/2011 |

OTHER PUBLICATIONS

Unofficial English translation of Chinese Office Action and Search Report issued from corresponding CN Application No. 201310751943.3 dated Jun. 17, 2015.

* cited by examiner

*Primary Examiner* — Joel Lamprecht
(74) *Attorney, Agent, or Firm* — Dean D. Small; The Small Patent Law Group, LLC (57) ABSTRACT

Systems and methods for ultrasound image rendering are provided. One system includes a user interface having a display configured to display ultrasound images for a volume data set and a content detection module configured to detect an object within the volume data set. The system also includes an image-processing module configured to receive ultrasound signals from a diagnostic probe and process the signals to generate the ultrasound images. The image-processing module is further configured to locally change an opacity function of the displayed ultrasound image based on the detected object to change an opacity of a subset of voxels in the volume data set.

22 Claims, 7 Drawing Sheets

SYSTEMS AND METHODS FOR ULTRASOUND IMAGE RENDERING

BACKGROUND

The subject matter disclosed herein relates generally to medical imaging systems, and more particularly to rendering images using ultrasound imaging systems.

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device.

During an imaging session, the operator typically views an imaging screen, which includes an ultrasound image. For instance, the ultrasound image may be in real-time, a recorded cine movie, or an ultrasound still frame. For some imaging sessions, a particular area or object in the displayed image(s) may be of more interest or have more importance than another area or object. For example, during a guided medical procedure where a medical device (e.g., a catheter, prosthesis or mitral-clip) is used, the visibility of the medical device is of particular interest during placement to ensure proper guidance and positioning. Accordingly, during rendering of the ultrasound images, for example, three-dimensional (3D) ultrasound images, some structures or objects are more desirably viewed clearly than other structures or objects.

However, some objects, such as the medical devices, can create shadows within a region of interest due to the reflection of the ultrasound waves from the objects. As a result, it can be more difficult to understand or interpret the displayed images, which can lead to difficulty or errors, such as during guidance and placement of a device. In some instances, portions of the object may be hidden and/or other portions of the object may be very bright (e.g., reflecting all ultrasound echoes), thereby also affecting viewing of the images.

Thus, in conventional ultrasound volume rendering techniques, the visibility of devices may be obstructed or may cause visual impairments in the images.

BRIEF DESCRIPTION

In one embodiment, an ultrasound imaging system is provided that includes a user interface having a display configured to display ultrasound images for a volume data set and a content detection module configured to detect an object within the volume data set. The ultrasound imaging system also includes an image-processing module configured to receive ultrasound signals from a diagnostic probe and process the signals to generate the ultrasound images. The image-processing module is further configured to locally change an opacity function of the displayed ultrasound image based on the detected object to change an opacity of a subset of voxels in the volume data set.

In another embodiment, a method of imaging a subject using an ultrasound imaging system is provided. The method includes processing ultrasound data within a volume data set to generate ultrasound images, wherein the ultrasound images include an acquired image and the acquired image includes an object of interest. The method also includes identifying the object of interest in the volume data set and locally changing an opacity function of the displayed ultrasound image based on the detected object to change an opacity of a subset of voxels in the volume data set to generate an image having an enhanced visualization of the object of interest.

DETAILED DESCRIPTION

Embodiments described herein include systems, methods, and computer readable media that may provide an improved and/or adaptive rendering of image data sets based on one or more objects or structures being displayed. For example, embodiments described herein may adaptively render a three-dimensional (3D) ultrasound data set based on detection of content within the data set, such as one or more objects or structures (e.g., a catheter, prosthesis or mitral-clip, or tissue) within the data set, which in some embodiments includes changing the opacity of portions of the rendered image. In some embodiments, the opacity function is dynamically changed. Thus, one or more regions or objects may be made to appear partially transparent (e.g., translucent) so that the operator may continue to be aware or otherwise cognizant of (or be able to better understand or interpret) other regions or areas of the ultrasound image.

At least one technical effect of various embodiments is enhanced or improved viewing of a region in a rendered image, such as device or tissue within the image. It should be noted that although the various embodiments are described in connection with a medical ultrasound imaging system, the various embodiments may be implemented in connection with a non-medical ultrasound imaging system (e.g., an industrial inspection system) or a non-ultrasound system.

The following detailed description of various embodiments will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
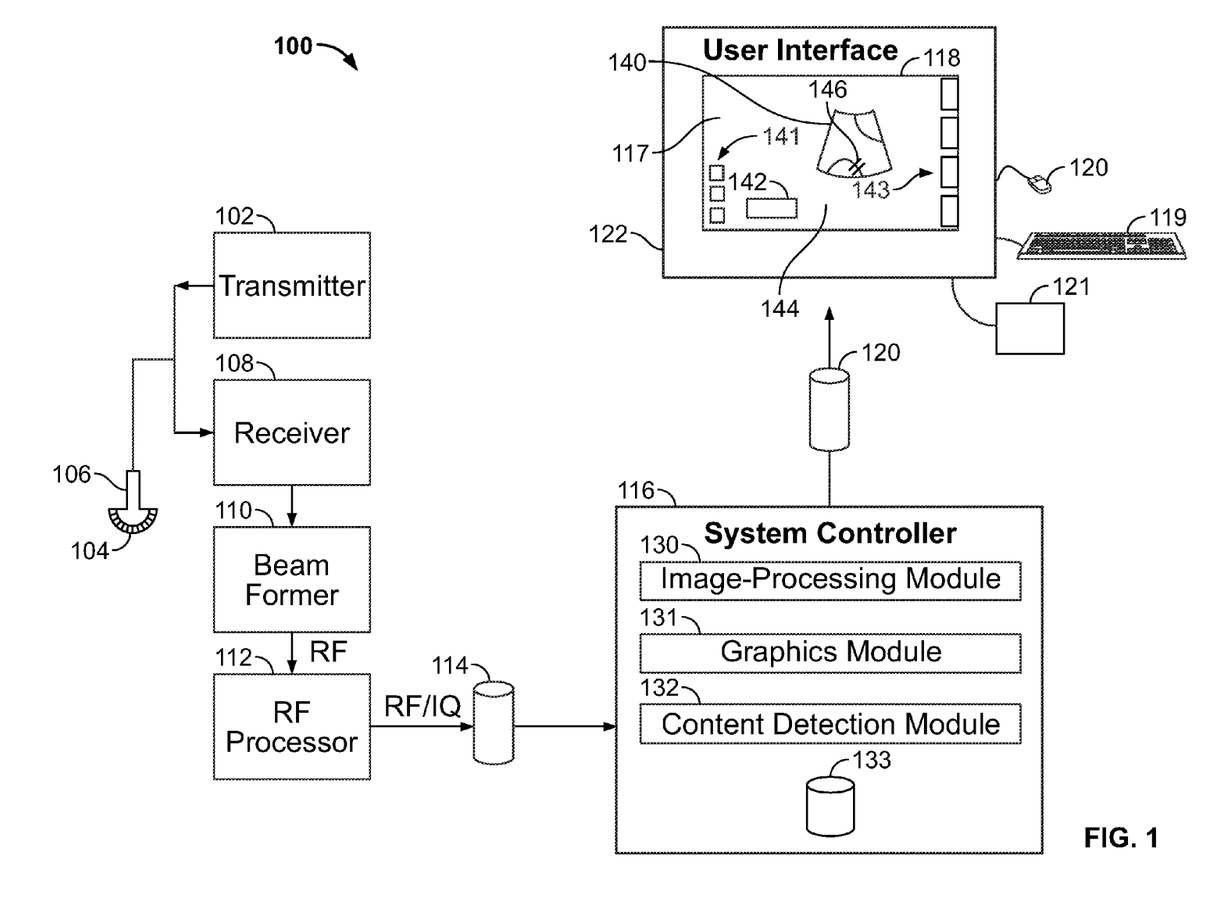
FIG. 1 illustrates a block diagram of an ultrasound imaging system in accordance with one embodiment.

FIG. 1 illustrates a block diagram of an ultrasound system 100 according to one embodiment. The ultrasound system 100 may be a unitary apparatus such that the elements and components of the system 100 may be carried or moved with each other. The ultrasound systems 300, 350, 400 shown in FIGS. 7, 8, and 9, respectively, illustrate examples of such systems. However, in other embodiments, at least one of the system components and elements described herein may be located remotely with respect to other components and elements. For example, one or more of the described modules may operate in a data server that has a distinct and remote location with respect to an ultrasound probe and the user interface.

In the illustrated embodiment, the ultrasound system 100 includes a transmitter 102 that drives an array of elements 104, for example, piezoelectric crystals, within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood cells or muscular tissue, to produce echoes that return to the elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage). In the illustrated embodiment, the probe 106 is only configured for imaging. In other embodiments, the probe 106 may also be configured to provide therapy through, for example, high-intensity focused ultrasound (HIFU).

The ultrasound system 100 also includes a system controller 116 that includes a plurality of modules. The system controller 116 is configured to control operation of the ultrasound system 100. For example, the system controller 116 may include an image-processing module 130 that receives the ultrasound signals (e.g., RF signal data or IQ data pairs) and processes the ultrasound signals to generate frames of ultrasound information (e.g., ultrasound images) for displaying to the operator. The image-processing module 130 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D), three-dimensional (3D) or four-dimensional (4D).

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed frames of acquired ultrasound information that are not scheduled to be displayed immediately. The image memory 120 may comprise any known data storage medium, for example, a permanent storage medium, removable storage medium, and the like.

In operation, the ultrasound system 100 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, and the like). Ultrasound images are displayed to the operator or user of the ultrasound system 100 on the display device 118.

The system controller 116 is operably connected to a user interface 122 that enables an operator to control at least some of the operations of the image-processing module 130. The user interface 122 may include hardware, firmware, software, or a combination thereof that enables an individual (e.g., an operator) to directly or indirectly control operation of the ultrasound system 100 and the various components thereof. As shown, the user interface 122 includes a display device 118 having a display area 117. In some embodiments, the user interface 122 may also include one or more input devices, such as a physical keyboard 119, mouse 120, and/or touchpad 121. In one embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information to the operator by displaying the information to the operator. The display device 118 and/or the user interface 122 may also be configured to receive audible inputs or commands. The display device 118 is configured to present information to the operator during the imaging session. The information presented may include ultrasound images, graphical elements, user-selectable elements, and other information (e.g., administrative information, personal information of the patient, and the like).

The system controller 116 also includes a graphics module 131, a content detection module 132, and a database 133. The image-processing module 130, the graphics module 131, and the content detection module 132 coordinate with one another to present information to the operator during the imaging session. For example, the image-processing module 130 may be configured to generate for display an acquired image 140 on the display device 118, and the graphics module 131 may be configured to display designated graphics along with the ultrasound images. The graphics may include icons 141, data fields 142, user-selectable elements 143, and the like.

The content detection module 132 is configured to detect content or features, such as objects or areas within the acquired ultrasound data, which is then used by the image-processing module 130 to adaptively render the displayed image 140 based on the detection of the content (e.g., a catheter, prosthesis or mitral-clip, or tissue), which may be detected automatically, semi-automatically or manually as described in more detail herein. For example, in some embodiments, based on the detected content or feature, such as an object or region of interest, an opacity function for the detected content or feature (or surrounding area) is dynamically changed, such as to allow enhanced or improved viewing of the content or feature within the displayed image 140. For example, a local (versus universal or global) change to the opacity value of a plurality of pixels or voxels (which is a subset of the all of the pixels or voxels forming the displayed image 140 in various embodiments) is performed to make the object or region of interest (or surrounding area) appear more or less visible (e.g., more or less transparent). It should be noted that in other embodiments, the display or rendering parameters of regions that are obstructing the object or region of interest may be adjusted (e.g., made to appear more transparent) to allow enhanced or improved viewing of the object or region of interest. It should be noted that in various embodiments, the display and/or rendering parameters are adjusted, but the acquisition parameters are not adjusted.

Thus, in various embodiments, the opacity of a portion of the displayed image 140 is changed (local change) and not the opacity of the entire displayed image (global change). Accordingly, in various embodiments the assigned gray level intensity for a plurality of voxels is changed or assigned per voxel, for some but not all of the voxels forming the displayed image 140. For example, in various embodiments, intensity to opacity mapping is performed using a opacity function curve that is applied locally to one or more portions of the displayed image 140 and not to the entire displayed image 140.

Thus, various embodiments may improve the representation and the rendering of 3D medical images by detecting an object of interest in the volume, with the detection then used to locally modulate the opacity function of the rendering in order to make the object of interest more prominent or less visible (or even transparent). For example, in the field of interventions, where devices are inserted into the body, during some phases, the devices within the subject's body should be clearly visible to the user, whereas at other time the devices may obstruct some other structures. The image-processing module 130 performs adaptive rendering to dynamically change display and/or rendering parameters, which in various embodiments, are opacity settings, to cause regions or object to appear more or less visible.

The rendering of the displayed image 140 in accordance with various embodiments may facilitate the operator during the imaging session by displaying the information of interest at the particular time to allow, for example, for placement or positioning of device within the subject. For example, FIG. 1 illustrates an imaging screen 144. During an imaging stage (or a review stage), the content detection module 132 may identify a region or area of interest within a 3D acquired image volume that the image-processing module 130 renders (with locally varying display or rendering parameters, such as to an object 146), and the appropriate graphics from the graphics module 131, and the appropriate information from the database 133 to display. In FIG. 1, the imaging screen 144 includes the ultrasound image 140, the icons 141, and the user-selectable elements 143.

It should be noted that the operator may be enabled to activate one of the user-selectable elements 143 to, for example, make adjustments to the displayed image 140 or to select different images. In the displayed image 140, the object 146 or surrounding tissue may, for example, have an adjusted opacity setting such that the object 146 or tissue made to appear more or less transparent, such as partially transparent in the displayed image 140. As such, the operator may remain aware or may be more cognizant or be able to better identify the object 146 in the displayed image 140 (e.g., view the entire object 146) or surrounding area while other operations are executed or performed, such as moving the object 140 within the subject. It should be noted that in some embodiments, multiple different levels of opacity adjustment may be performed to one or more different regions or areas within the displayed image 140 (e.g., the object 146 and the tissue surrounding the object 146).

Figure 2:
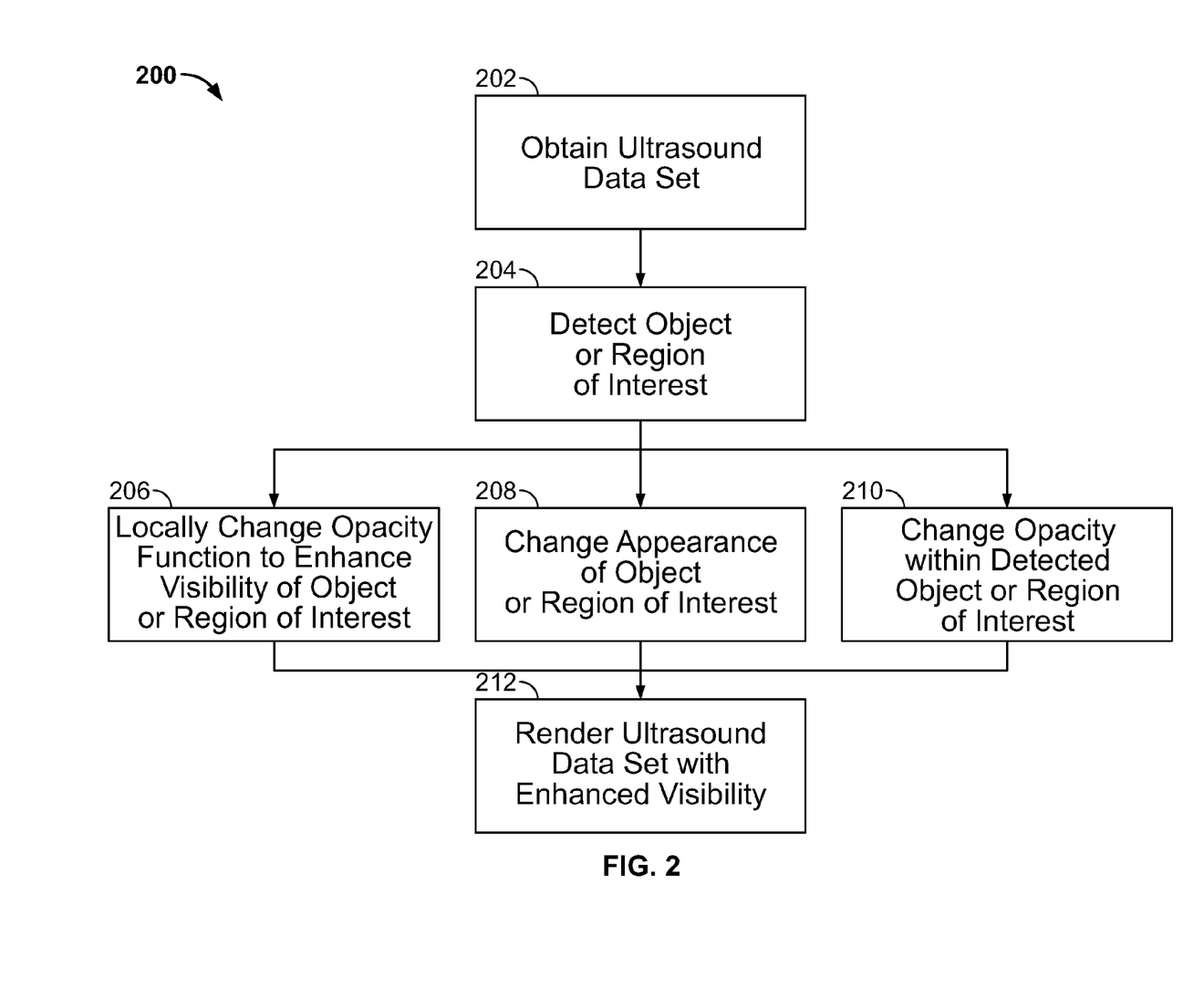
FIG. 2 is a flowchart of a method according to one embodiment for adaptive image rendering.

FIG. 2 is a flowchart of a method 200 of imaging a subject using an ultrasound imaging system, such as the ultrasound systems 100, 300, 350, and 400 (FIGS. 1, 7, 8, and 9, respectively). For example, the method 200 in some embodiments provides adaptive rendering of 3D data sets of a volume of interest of the subject based on detecting an object or feature of interest. The method 200 includes obtaining an ultrasound data set at 202, which in various embodiments is a 3D ultrasound data. It should be noted that the data may be obtained from a current scanning session, such as live or real-time or from a stored data set previously acquired.

The method 200 also includes detecting an object or region of interest within the ultrasound data set at 204, such as using one or more detection methods described herein. For example, in the illustrated embodiment, the object of interest is a device, such as a medical device inserted within the subject. The detection may be performed automatically, semi-automatically or manually. For example, the detection may be fully automatic by applying segmentation methods such as thresholding or border detection methods to identity objects having a particular shape or size, which may be based on, for example, a type of examination or a user input object of interest (e.g., catheter). For example, in the case of a catheter, various embodiments search for a thick long structure within the data set. However, any suitable image processing and/or object detection technique may be used, for example, a pattern recognition technique, correlation, statistical analysis or linear regression approach may be used to identify the object of interest.

Figure 3:
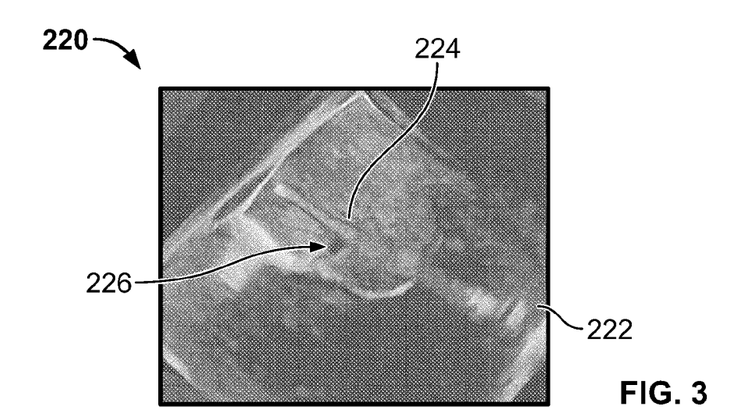
FIG. 3 illustrates an ultrasound image that may be adaptively rendered in accordance with various embodiments.

For example, FIG. 3 illustrates an ultrasound image 220 of a rendered 3D volume 222 that may be displayed on the display device 118 (shown in FIG. 1). In some embodiments, a series of images 220 may be displayed over time, such as in 4D trans-esophageal echocardiographic imaging. The ultrasound image 220 is of a heart showing a catheter 224 passing through an opening 226 in the left atrial wall. As can be seen, the portion of the imaged catheter 224 on the left side of the opening 226 (as viewed in FIG. 3) is visible and can be identified (e.g., clearly delineated), while the portion of the imaged catheter 224 on the right side of the opening 226 (as viewed in FIG. 3) is blurred.

In some embodiments, a linear regression approach or maximum likelihood technique may be used to identify the catheter 224 in the ultrasound data set 222. For example, in various embodiments, the catheter 224 is assumed to be straight in 3D. With the thickness of the catheter 224 known, an object recognition algorithm may be used to locate and identify a line of higher intensity ultrasound echo signals. The identified line is then determined to be the catheter 224 within the image 220.

In other embodiments, the detection of the object or region of interest, which in this embodiment, is the catheter 224, may be performed semi-automatically, such as with the user providing information about the structure (the catheter 224 in this example) for use in the detection process. For example, a user may input the dimensions (or property or characteristic) of the catheter 224 and then various embodiments perform a search for an object matching or approximating the dimensions (e.g., search for an object having a known length and width). In some embodiments, the user input may include selecting from a list of devices, the device that is being used. In one embodiment, the list includes the properties and characteristics of the device being used such as size and shape (e.g., for an Amplatzer device), with that information used during the detection process (e.g., to locate an object in the image having the same or approximately the same dimensions or shape).

In some embodiments, a maximum likelihood approach may be used to identify the location of the catheter 224. In other semi-automatic embodiments, a user may, for example, interact with the data set, such as by selecting on the display the start or end of the catheter 224. Various examples of user interaction include, but are not limited to: clicking on the data to indicate one or several voxels belonging to the device (which will be used to position a model and then a region-growing segmentation is performed) or also positioning a CAD model of the device by indicating a few points and/or orientation information. In other embodiments, a manual approach may be used. For example, in some embodiments, detouring may be used, meaning a user draws the contour of the device on the display. It should be noted that the detection at 204 may be performed using a single image frame or multiple image frames (e.g., real-time at least during a period that does not include too drastic changes of the image data, such as large motion of the imaging probe). Thus, it should be appreciated that different processes and techniques may be used to identify the object or region of interest in various embodiments, which is not limited to the processes and techniques described herein.

The method 200 then includes adaptively rendering the data set based on the detection at 204. The adaptive rendering may be performed in different ways and using different techniques as described herein. For example, the adaptive rendering at steps 206, 208, and/or 210 may be performed. It should be noted that only one of these steps may be performed or multiple ones of the steps may be performed. Additionally, a combination of the steps 206, 208 and 210 may be performed. It also should be noted that the steps 206, 208 and/or 210, if more than one is performed, may be performed, simultaneously, concurrently or sequentially.

The adaptive rendering may include locally changing the opacity function to enhance the visibility of the object or region of interest at 206. For example, in some embodiments, the opacity function is locally or regionally changed in order to make the device, in this example the catheter 224, more visible. For example, in one embodiment, after the catheter 224 is identified, the tissue around the catheter 224 is made semi-transparent by decreasing the opacity of the corresponding voxels in the data set. For example, the voxels within a predetermined distance of the edge of the catheter 224 are made semi-transparent by decreasing the opacity (e.g., by decreasing the intensity value) of the voxels. In some embodiments, the opacity is changed as a function of the distance from the edge of the catheter 224. For example, voxels farther from the catheter 224 are made more transparent (e.g., having a greater change in the opacity function value). Alternatively, and as another example, only the tissue in-front of the catheter 224, for example, in between the viewing point and the catheter 224, are made more transparent. Thus, in this embodiment, the tissue voxels around the catheter 224, which may be within a predetermined or defined distance around the catheter 224 are made to appear more transparent. Accordingly, the local or regional opacity of the tissue voxels surrounding the catheter 224 are changed to allow more of the catheter 224 to be viewed (e.g., not obstructed by tissue). Thus, in various embodiments, a subset of voxels less than all of the displayed voxels or less than all of the voxels in the data set have a change in opacity.

In various embodiments, the change in the opacity setting is a local or regional change in the opacity values of the voxels corresponding to the tissue voxels. The change may be based on a determined or defined change or may be user selected. For example, the opacity values may be changed a predetermined percentage, such as 75%, 50% or 25% or stepwise or gradually as described herein. In other embodiments, the opacity of the voxels may be changed based on a user input. For example, a slider bar may be displayed that allows a user to change the local or regional opacity of the voxels surrounding the catheter 224 (or other voxels as described herein). For example, the user may slide the virtually displayed bar that changes the transparency or translucency of the surrounding voxels. As another example, in some embodiments, the user is able to manipulate the opacity function (opacity as a function of intensity) by interacting with the opacity curve directly (e.g., changing properties or shape of the opacity curve).

Figure 6:
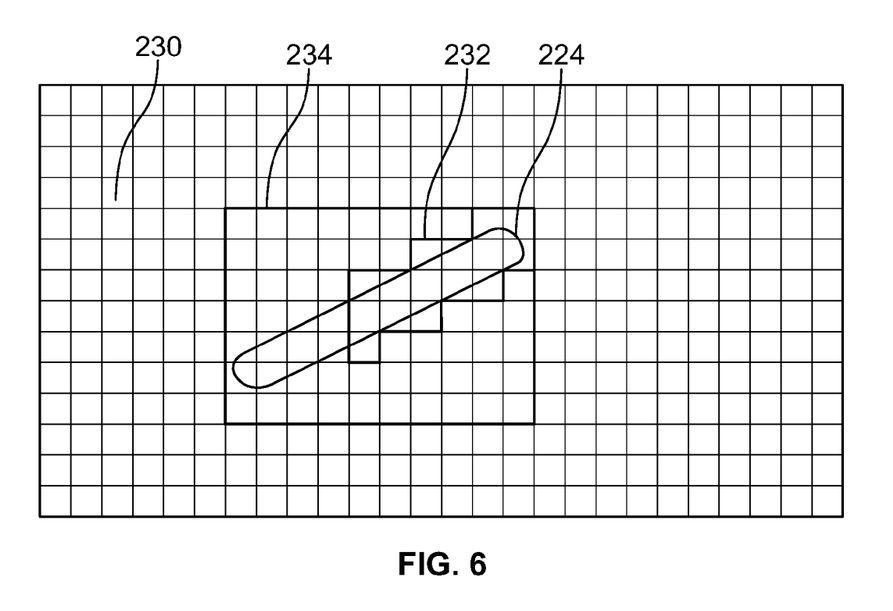
FIG. 6 is a diagram illustrating changing opacity values of voxels in accordance with various embodiments.

Thus, as illustrated in FIG. 6, showing a plurality of voxels 230 of the data set, the opacity of a number of voxels 230, which may be a defined number or at a defined distance, is changed, which may be changed the same amount or a different amount. For example, the opacity values for voxels 230 within a local region 232 may be changed. For example, the opacity values may be changed locally in the region 232 which does not include the entire catheter 224, but instead, that portion of the catheter 224 that is obstructed. For example, a determination may be made as to which voxels are blurred as not having passed through the opening 226 as shown in FIG. 3. In other embodiments, the opacity values are regionally changed, such as in an area 234 that includes voxels surrounding the entire catheter 224. It should be noted that the relative size of the voxels 230 to the catheter 224 has been increased for ease in illustration.

It also should be noted that the opacity mapping and defining of opacity values may be performed using suitable imaging or rendering techniques. For example, an opacity-weighted transfer function may be used to generate the RGB values for the voxels and an opacity function is used to generate the alpha values for the voxels. Accordingly, during volume rendering, each voxel intensity value in the data set volume is associated with an opacity value. The opacity value may be computed by applying a transfer function or other suitable function to the input values, which may include applying a different opacity curve locally or regionally.

The adaptive rendering may alternatively or optionally include changing an appearance of the object or region of interest at 208. For example, the appearance of the identified catheter 224 may be changed. For example, in various embodiments, the visibility of the displayed device, in this example the catheter 224, is increased or enhanced, such as by incorporating a mesh/surface representation of a 3D model of the catheter 224. In some embodiments, the region within the boundary of the catheter 224 is, for example, highlighted, colored, textured or otherwise modified to show inside the volume data set the location of the detected catheter 224. In some embodiments, the mesh is a representation of the catheter 224 (e.g., an overlay on the identified region of the catheter 224). In some embodiments, the 3D model is a CAD model, which may be automatically detected or selected or indicated by the user.

For example, in some embodiments, the voxels for the region of the identified catheter 224 are modified to change the appearance thereof. In some embodiments, the voxels are differently colored or highlighted to visually distinguish the catheter 224 from the surrounding tissue. In other embodiments, the region of the identified catheter 224 is overlaid with a model or representation of a catheter device. It should be noted that the model or representation is some embodiments is an approximation of the shape and/or size of the catheter 224. For example, the overlay may be a graphic representation, which may be colored or highlighted to enhance the delineation of the catheter 224 from the surrounding tissue. In some embodiments, optionally or alternatively to changing the opacity, the appearance of some voxels may be changed by changing locally one or more other parameters of the rendering algorithm, such as shading, smoothness and/or reflectivity, among others.

The adaptive rendering may alternatively or optionally include changing the opacity within the detected object or region of interest at 210. For example, instead of or in addition to changing the opacity of the voxels surrounding the catheter 224 (as performed at 206), the voxels within the catheter 224 are changed (with the voxels surrounding the catheter 224 having unchanged voxels in some embodiments). For example, the opacity of the voxels within the catheter 224 may be changed to make the catheter 224 appear less transparent, such as darker or brighter in some embodiments.

Accordingly, different regions or areas of the displayed image may be modified based on a detected object or region of interest, which may include changing the opacity of the area surrounding the detected object or region of interest, or changing the opacity of the detected object or region of interest. For example, during a navigational guidance procedure, it may be desirable to view the catheter 224 or other device (e.g., biopsy needle) during some portions of the procedure and desirable to view the surrounding area, including behind the catheter 224 during other portions of the procedure. Using various embodiments, the opacity or other display or rendering parameters may be changed based on the identified object or region of interest.

It should be noted that the adaptive rendering performed at 206, 208 and/or 210 may be performed independently or in different combinations. Additionally, different adaptive rendering may be performed and the processes described at 206, 208 and 210 are merely exemplary. For example, in some embodiments, the opacity of the voxels within the catheter 224 may be increased such that the catheter 224 appears more transparent, allowing viewing of voxels obstructed by the catheter 224 (e.g., voxels behind the catheter 224). This, instead of making the catheter 224 more visible, the visibility of the catheter 224 may be reduced or decreased by locally changing the opacity function of the catheter 224 in order to better view structures or tissue that are behind the catheter 224 for the current viewing position and direction.

The method 200 also includes at 212 rendering the ultrasound data set with enhanced visibility. For example, as described in more detail herein, the opacity of an identified object or region of interest and/or the surrounding region may be changed to allow improved or unobstructed viewing of the identified object or region of interest and/or the surrounding region. It should be noted that as, for example, the device moves, corresponding voxels may be adjusted accordingly.

Thus, the various embodiments provide for enhanced or improved visibility of an object or region of interest in data set volumes. The enhanced viewing may be provided without complex interaction, such as advanced cropping techniques using complex non-planar structures. It should be noted that although various embodiments are described in connection with particular interventional techniques using specific devices, the various embodiments may be used to detect any object or region of interest and provide enhance or improved visualization.

Figure 4:
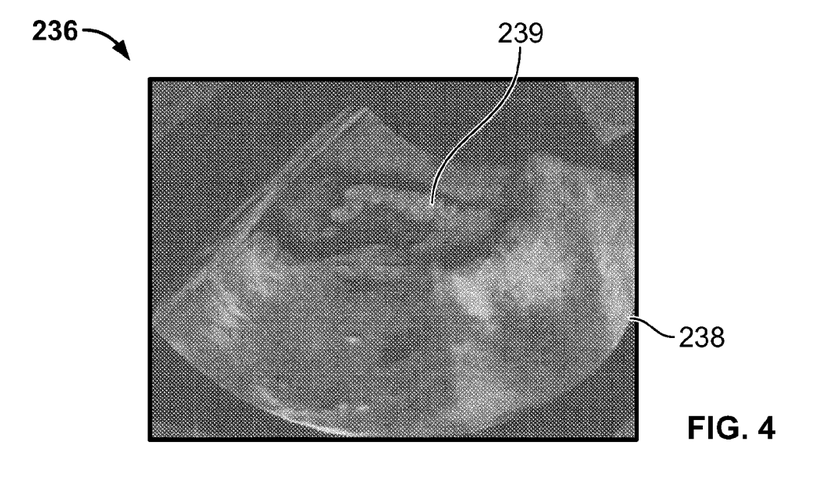
FIG. 4 illustrates another ultrasound image that may be adaptively rendered in accordance with various embodiments.

For example, referring again to the ultrasound image 220 shown in FIG. 3, the catheter 224 appears non-uniform in thickness due to blurring on the right side of the opening 226 (as viewed in FIG. 3). In particular, the displayed portion of the catheter 224 on the right side of the opening 226 is obstructed by tissue voxels. Accordingly, in some embodiments, the local opacity of voxels surrounding the catheter 224 (e.g., in front of the catheter 224) that cause blurring of the catheter 224, are modified, such as to make the voxels appear for transparent. This local changing of the opacity allows, for example, a user to better view the catheter 224 for positioning in a specific portion of the heart. However, as described in more detail herein, it may be desirable to view tissue voxels. For example, in such a case, the portion of the catheter 224 to the left of the opening 226 is made more transparent to allow viewing of the tissue voxels behind the catheter 224. Similar opacity changes may be made to the ultrasound image 236 of the volume 238 shown in FIG. 4 having an obstructed catheter 239. However, in this image 236, the entire catheter 239 is obstructed as illustrated by the blurring of the catheter 239. Accordingly, in this case, the opacity of the voxels surrounding or in front of the length of the catheter 239 may be changed.

Figure 5:
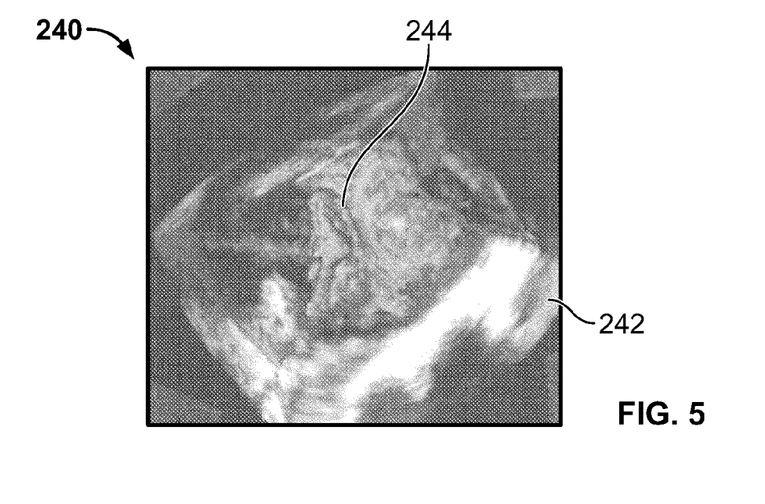
FIG. 5 illustrates another ultrasound image that may be adaptively rendered in accordance with various embodiments.

It should be noted that similar opacity changes may be made in connection with imaging other types of devices. For example, the ultrasound image 240 of the volume 242 shows an AMPLATZER Septal Occluder (ASO) device 244 designed for minimally-invasive atrial septal defect (ASD) closure. In this embodiment, the object detection, for example, performed at 204 of the method 200 (shown in FIG. 2), may include searching for an umbrella shaped device instead of a straight device as in the case of a catheter. The various methods of changing the opacity may be performed similarly as described in connection with the catheter.

Figure 7:
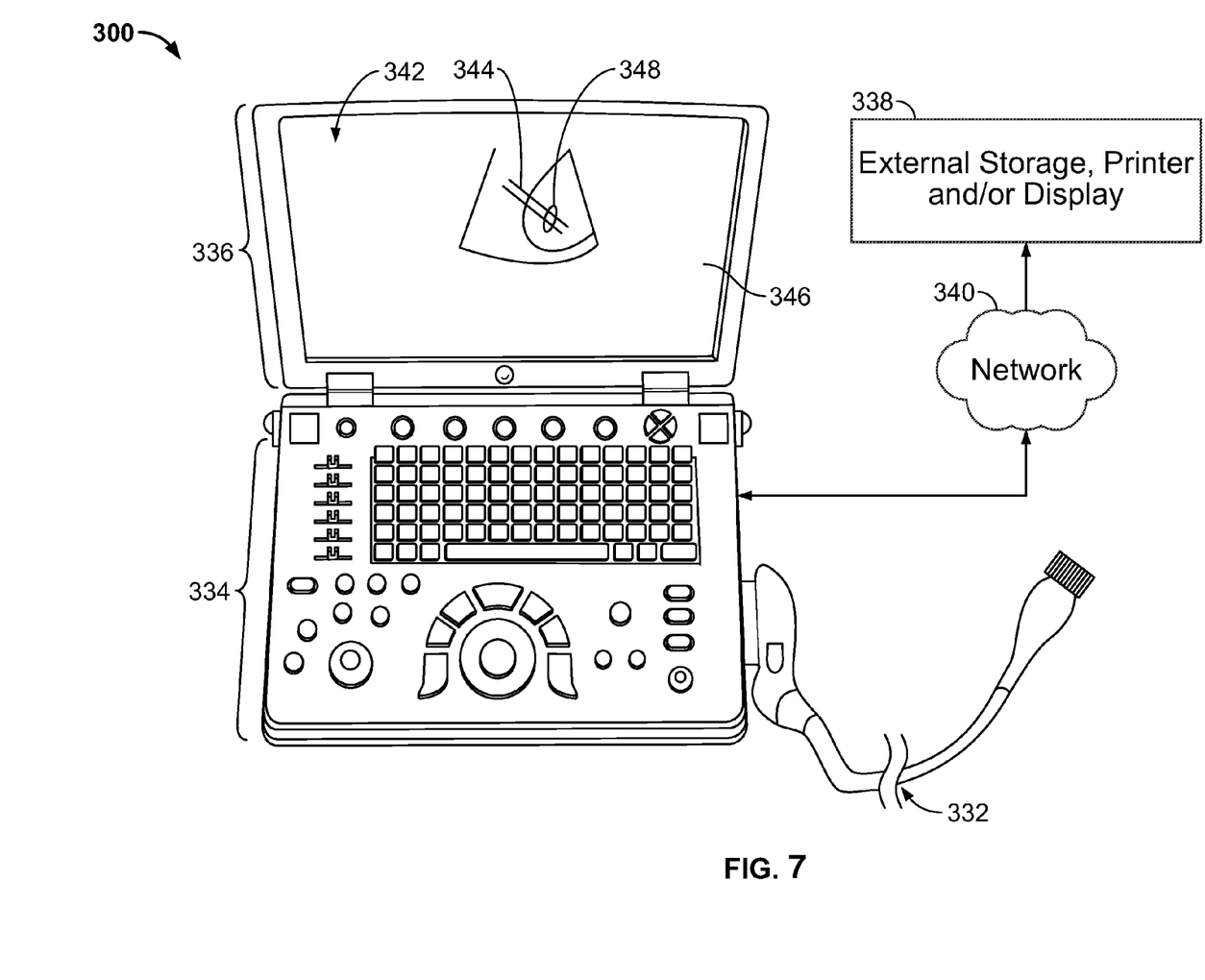
FIG. 7 illustrates an ultrasound system in which various embodiments may be implemented.

FIG. 7 illustrates a portable ultrasound system 300 having an ultrasound transducer 332 that may be configured to acquire ultrasonic data. For example, the ultrasound transducer 332 may have a 2D array of acoustic elements. A user interface 334 (that may also include an integrated display 336) is provided to receive commands from an operator. As used herein, "portable" includes a handheld or hand-carried device that may be carried in a person's hand, pocket, briefcase-sized case, or backpack. For example, the ultrasound system 300 may be a hand-carried device having a size of a typical laptop computer. The integrated display 336 (e.g., an internal display) is configured to display, for example, one or more medical images. The ultrasonic data may be sent to an external device 338 via a wired or wireless network 340 (or direct connection, for example, via a serial or parallel cable or USB port). In some embodiments, the external device 338 may be a computing system (e.g., computer, server, and the like).

The display 336 may be configured to show an imaging screen and a transparent object or region of interest (or surrounding region) such as described above. For instance, the display 336 includes a display area 342 that is configured to display an acquired ultrasound image 344. In the illustrated embodiment, the visualization of a device 344 is enhanced by adaptive opacity changes to allow viewing of the entire device 344 on both sides of an opening 348 (including behind tissue that would otherwise cause blurring).

Figure 8:
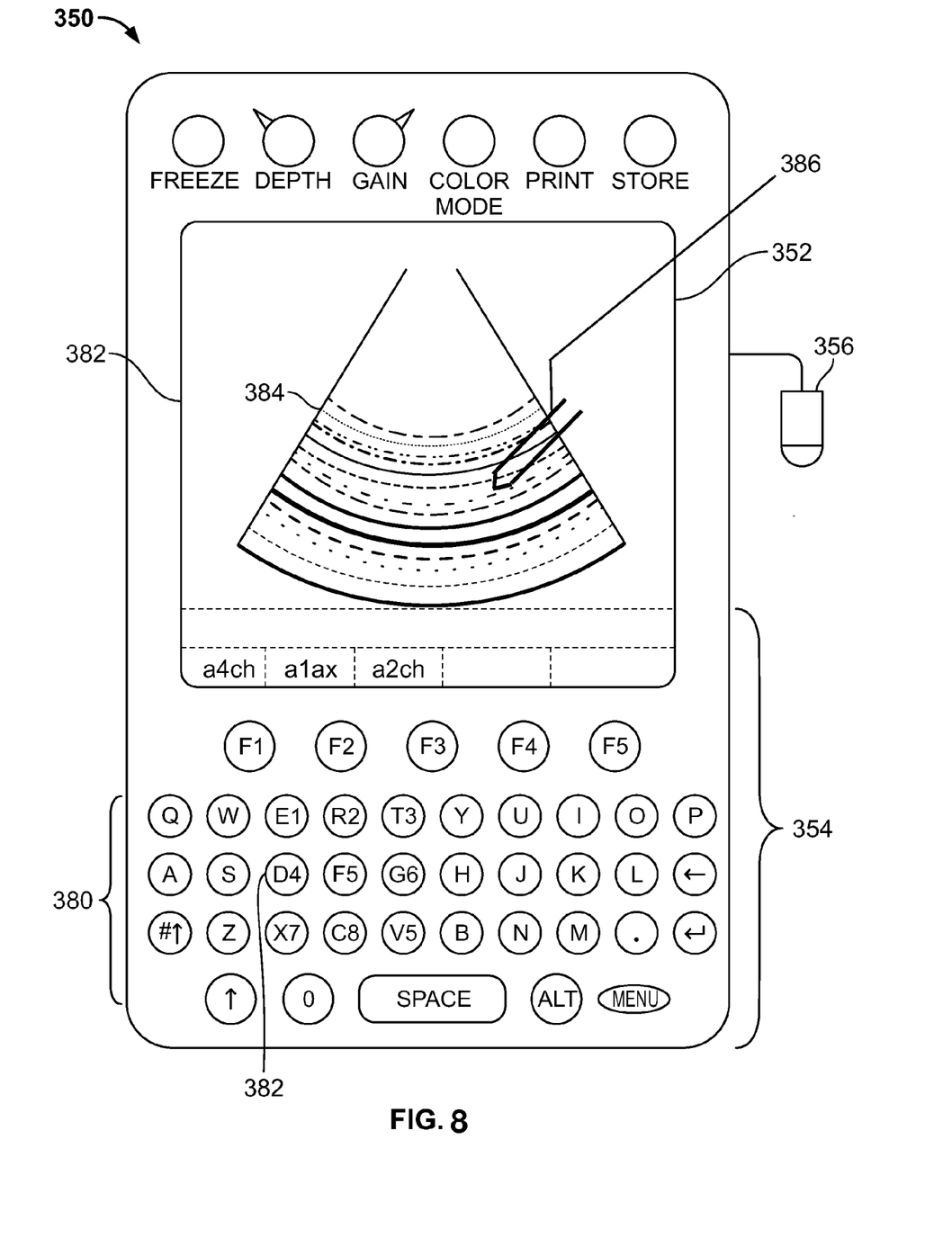
FIG. 8 illustrates a portable ultrasound imaging system in which various embodiments may be implemented.

FIG. 8 illustrates a portable hand-carried or pocket-sized ultrasound imaging system 350 wherein a display 352 and a user interface 354 form a single unit. By way of example, the pocket-sized ultrasound imaging system 350 may be a personal communication device, such as a smartphone or tablet. By way of example, the personal communication device may be dimensioned to be less than 3 inches wide, less than 4 inches in length, and less than 0.5 inches in depth, less than 8 ounces in weight. The portable ultrasound imaging system 350 generally includes the display 352, user interface 354, which may or may not include a keyboard-type interface and an input/output (I/O) port for connection to a scanning device, for example, and an ultrasound transducer 356. The display 352 may be, for example, a 320×320 pixel color LCD display (on which a medical image 390 may be displayed). A typewriter-like keyboard 380 of buttons 382 may optionally be included in the user interface 354. In other embodiments, the display 352 may be larger and a virtual keyboard may be shown.

In FIG. 8, the display 352 includes a display area 382 that includes an acquired image 384 and an identified device 386, which in this example has a changed appearance (e.g., a model or mesh overlay).

Figure 9:
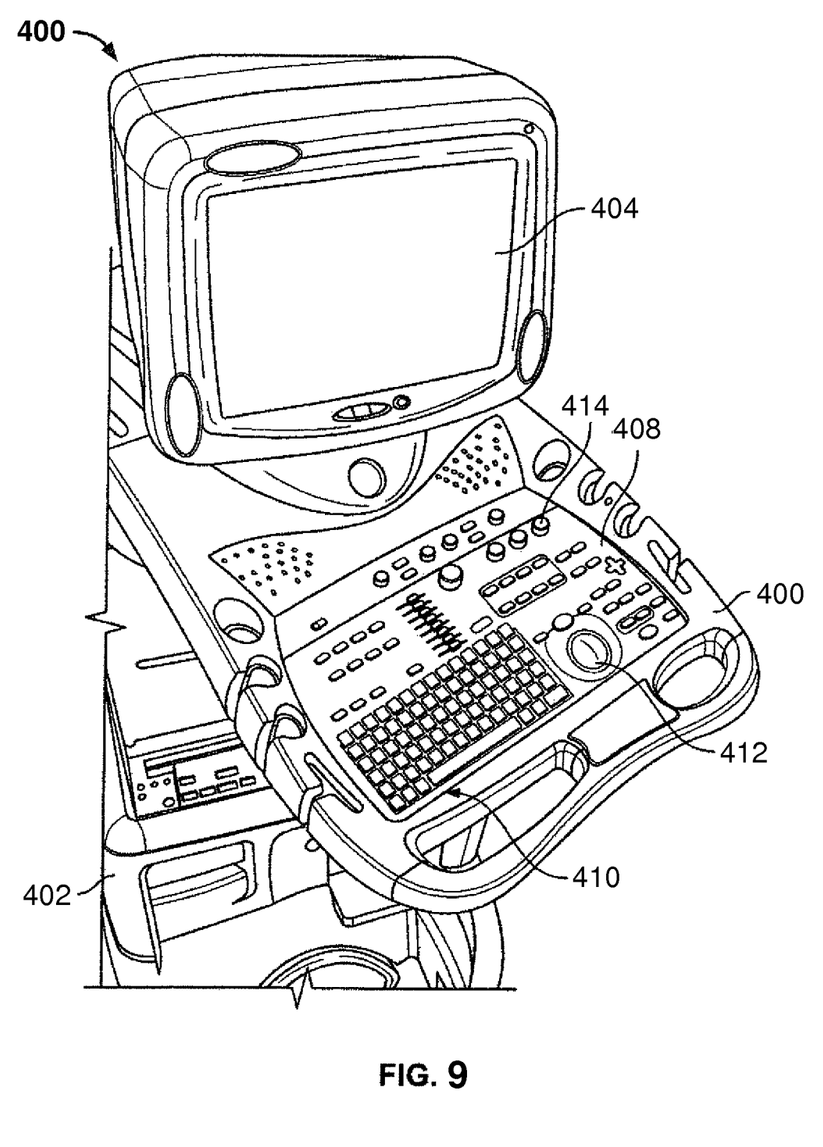
FIG. 9 illustrates a console-type ultrasound imaging system in which various embodiments may be implemented.

FIG. 9 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and/or the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that although one or more embodiments may be described in connection with an ultrasound system, the embodiments described herein are not limited to ultrasound systems. In particular, one or more embodiments may be implemented in connection with different types of medical imaging systems. Examples of such medical imaging systems include a magnetic resonance imaging (MRI) system, computed tomography (CT) system, positron emission tomography (PET) system, a PET/CT system, and single photon emission computed tomography (SPECT) system. In such embodiments, the acquired images may be MRI images, CT images, PET images, PET/CT images, and SPECT images.

As used herein, the term "computing system" or "system controller" may include any processor-based or microprocessor-based systems including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computing system" or "system controller."

Sets of instructions may include various commands that instruct the computing system or system controller as a processing machine to perform specific operations such as the methods and processes described herein. The set of instructions may be in the form of a software program or module. The software may be in various forms such as system software or application software. In some embodiments, a tangible and non-transitory computer readable medium is provided. Further, the software may be in the form of a collection of separate programs, a program module (or module) within a larger program, or a portion of a program module. The software also may include modular programming in the form of object-oriented programming. The processing of input data by the processing machine may be in response to user commands, or in response to results of previous processing, or in response to a request made by another processing machine. The program is configured to run on both 32-bit and 64-bit operating systems. A 32-bit operating system like Windows XP™ can only use up to 3 GB bytes of memory, while a 64-bit operating system like Window's Vista™ can use as many as 16 exabytes (16 billion GB). In some embodiments, the program is configured to be executed on a Linux-based system.

As used herein, the terms "software" and "firmware" are interchangeable, and include any computer program stored in memory for execution by a computing system, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of various embodiments, they are by no means limiting and are only example embodiments. Many other embodiments will be apparent to those of skill in the art upon reviewing the above description. The scope of the present application should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:
1. An ultrasound imaging system comprising:
a user interface having a display configured to display ultrasound images for a volume data set;

a content detection module configured to detect an object within the volume data set, wherein the detected object is a medical device; and an image-processing module configured to receive ultrasound signals from a diagnostic probe and process the signals to generate the ultrasound images of the volume data set, the image-processing module further configured to locally change an opacity function of the displayed ultrasound image based on the detected object to change an opacity of a subset of voxels in the volume data set that are within a defined distance from the detected object.

2. The ultrasound imaging system of claim 1, wherein the defined distance of the detected object is based on an edge of the detected object, wherein the local change causes the voxels to appear more transparent on the display.

3. The ultrasound imaging system of claim 1, wherein the image-processing module is further configured to change a displayed appearance of the detected object by overlaying a mesh or model representation of the detected object to the detected object displayed in the ultrasound image.

4. The ultrasound imaging system of claim 1, wherein the image-processing module is further configured to locally change an opacity function of voxels within the detected object to cause the detected object to appear less transparent on the display.

5. The ultrasound imaging system of claim 1, wherein the image-processing module is further configured to locally change an opacity function of voxels within the detected object to cause the detected object to appear more transparent on the display.

6. The ultrasound imaging system of claim 1, wherein the content detection module is further configured to detect the object using a received user input defining a property, dimension or characteristic of the object.

7. The ultrasound imaging system of claim 1, wherein the image-processing module is further configured to locally change an opacity function of the displayed ultrasound image based on the detected object to change an opacity of a plurality of subsets of voxels in the volume data set that are within a defined distance from the detected object, wherein the opacity change to at least two of the subsets of voxels is different based on a distance from the detected object.

8. The ultrasound imaging system of claim 1, wherein the image-processing module is further configured to locally change an opacity function of the displayed ultrasound image, the local change less than a global change of the opacity of all of the voxels in the volume data set.

9. The ultrasound imaging system of claim 1, wherein the image-processing module is further configured to change a displayed appearance of the detected object by changing locally at least one volume rendering parameter, including at least one of shading, reflectivity or smoothness.

10. A method of imaging a subject using an ultrasound imaging system, the method comprising:
processing ultrasound data within a volume data set to generate ultrasound images, the ultrasound images including an acquired image, the acquired image including an object of interest;
identifying the object of interest in the volume data set, wherein the detected object is a medical device; and
locally changing an opacity function of the displayed ultrasound image based on the detected object to change an opacity of a subset of voxels in the volume data set that are within a defined distance from the detected object to generate an image having an enhanced visualization of the object of interest.

11. The method of claim 10, wherein the identifying is performed automatically.

12. The method of claim 10, wherein the identifying is performed semi-automatically using a received user input defining at least one of a shape or dimension of the object of interest.

13. The method of claim 10, wherein the defined distance of the detected object is based on an edge of the detected object, wherein the local change causes the voxels to appear more transparent on the display.

14. The method of claim 10, further comprising changing a displayed appearance of the detected object by overlaying a mesh or model representation of the detected object to the detected object displayed in the ultrasound image.

15. The method of claim 10, wherein locally changing the opacity function comprises locally changing an opacity function of voxels within the detected object to cause the detected object to appear less transparent on the display.

16. The method of claim 10, wherein locally changing the opacity function comprises locally changing an opacity function of voxels within the detected object to cause the detected object to appear more transparent on the display.

17. The method of claim 10, wherein locally changing the opacity function comprises locally changing an opacity function of the displayed ultrasound image, the local change less than a global change of the opacity of all of the voxels in the volume data set.

18. A tangible non-transitory computer readable medium programmed to instruct a computing system to:
process ultrasound data within a volume data set to generate ultrasound images, the ultrasound images including an acquired image, the acquired image including an object of interest, wherein the object of interest is a medical device;
identify the object of interest in the volume data set; and
locally change an opacity function of the displayed ultrasound image based on the detected object to change an opacity of a subset of voxels in the volume data set that are within a defined distance from the detected object to generate an image having an enhanced visualization of the object of interest.

19. The computer readable medium of claim 18, wherein the defined distance of the detected object is based on an edge of the detected object, wherein the local change causes the voxels to appear more transparent on the display.

20. The computer readable medium of claim 18, wherein the computing system is instructed to change a displayed appearance of the detected object by overlaying a mesh or model representation of the detected object to the detected object.

21. The computer readable medium of claim 18, wherein the computing system is instructed to locally change an opacity function of voxels within the detected object to cause the detected object to appear less transparent on the display.

22. The computer readable medium of claim 18, wherein the computing system is instructed to locally change an opacity function of voxels within the detected object to cause the detected object to appear more transparent on the display.

* * * * *